United States Patent [19]

Henry

[11] 4,115,593
[45] Sep. 19, 1978

[54] PROCESS FOR PRODUCING FEED PROTEIN

[75] Inventor: Dick Peter Henry, Brookfield, Australia

[73] Assignee: The University of Queensland, St. Lucia, Australia

[21] Appl. No.: 866,909

[22] Filed: Jan. 4, 1978

Related U.S. Application Data

[63] Continuation of Ser. No. 744,338, Nov. 23, 1976, abandoned, which is a continuation of Ser. No. 621,577, Oct. 10, 1975, abandoned, which is a continuation of Ser. No. 476,838, Jun. 6, 1974, abandoned.

[30] Foreign Application Priority Data

Jun. 6, 1973 [AU] Australia .............................. 3561/73
Apr. 22, 1974 [AU] Australia .............................. 7314/74

[51] Int. Cl.$^2$ ................................................ A23K 1/00
[52] U.S. Cl. ........................................ 426/53; 195/82; 426/56; 426/60; 426/807

[58] Field of Search ...................... 195/82, 30, 88, 90; 210/2, 11, 12, 15; 426/60, 52, 55, 56, 53, 807

[56] References Cited

U.S. PATENT DOCUMENTS 3,383,309  5/1968  Chandler .............................. 195/96
3,775,252  11/1973  Kinsel et al. .......................... 195/30

OTHER PUBLICATIONS

Cook, "The Chemistry and Biology of Yeasts", Academic Press, 1958, pp. 26, 27, 37, 51 and 264–267.

Primary Examiner—R. B. Penland
Attorney, Agent, or Firm—Donald D. Jeffery

[57] ABSTRACT

A process for producing yeast protein from biological waste material includes preliminary anaerobic fermentation of said material, inoculation with a pellicle-forming yeast growing as a surface layer, and skimming off and drying said surface layer. Specific yeasts are *CANDIDA INGENS* and *PICHIA MEMBRANAEFACIENS*.

4 Claims, No Drawings

PROCESS FOR PRODUCING FEED PROTEIN

This is a continuation of application Ser. No. 744,338, filed Nov. 23, 1976, now abandoned, which is in turn a continuation of Ser. No. 621,577, filed Oct. 10, 1975, now abandoned, which in turn is a continuation of Ser. No. 476,838, filed June 6, 1974, also now abandoned.

This invention relates to the production of protein from yeast growth on biological waste material.

It has been known to grow certain micro-organisms on sewerage wastes, including farm wastes. However, the yields have either not been suitable for animal feed, or have been of too high a cost or too low a yield to be economical.

An object of this invention is to provide a protein ingredient for incorporation in stock feed at low cost and high yield by a process using a specific type of yeast.

In previous yeast culture in biological waste material, one of the difficulties has been in harvesting the yeast product. The yeast then used grew throughout the mix. Aeration of the mix was necessary and subsequent separation of the mixed product by centrifugation or filtering.

A further object of this invention is to provide easy separation of the yeast from the growth medium.

The invention comprises a process of producing yeast protein including the following steps:
(a) subjecting biological waste material to anaerobic fermentation;
(b) introducing yeast into said fermented material, the yeast being a pellicle-forming yeast growing as a surface layer;
(c) allowing a surface layer of said yeast to grow on said material;
(d) skimming off said surface layer; and
(e) drying said skimmed yeast to form said yeast protein.

The dried yeast is preferably milled to a powder suitable for incorporation in a stock feed.

The invention, in another aspect, comprises a stock feed when produced by the above process.

The yeast product forms as a surface layer of wrinkled pellicles only, and is not produced throughout the mass.

No vigorous stirring nor aeration is necessary or desirable, though very gentle stirring sufficient to circulate the substrate to and from the surface layer, but not to disturb it, is an advantage.

Separation is by simple skimming off of the yeast and draining, which gives a clean product which when dehydrated gives a brittle grey-white crust, the yeast of course being killed.

The yeasts used in the process are pellicle-forming yeasts capable of growing as a surface layer as described.

Examples are *Candida ingens* and *Pichia membranaefaciens*, though a considerable number of as yet unidentified pellicle-forming surface yeasts have been found to be effective.

The anaerobic aqueous fermentation may be of a variety of biological waste materials.

Examples are; pig wastes, yellow straw such as wheat straw; food wastes; animal, including human faeces.

The anaerobic fermentation produces a series of volatile mono-carboxylic fatty acids (abbreviated VFA) which in the presence of nitrogen act as feed for yeast growth.

Animal wastes usually provide sufficient nitrogen, but some materials may need addition of nitrogenous matter, such as urine.

The amount of available nitrogen should be of the order of 1000 mg/liter.

It is found that the yeasts at atmospheric temperatures of some 25°–28° C., and with gentle stirring to give the whole substrate access to the surface layer, come to maximum growth in from 24 to 48 hours.

The longer-chain fatty acids produced by the anaerobic fermentation are taken up by the yeast in preference to the shorter-chain ones.

For example, where the fermentation was of raw pig wastes, the following percentage reduction of the various fatty acids were as in column 1 below. Where the wastes were autoclaved, the corresponding percentages were as in column 2:

|  | Col. 1 (%) | Col. 2 (%) |
| --- | --- | --- |
| Acetic acid | 31.4 | 44.4 |
| propionic ac. | 53.9 | 46.3 |
| Butyric | 78.8 | 70.2 |
| Iso-valeric | 65.3 | 47.6 |
| Valeric | 86.5 | 63.8 |
| Caproic | 100 | 75.0 |

It will be seen that utilization is less in the autoclaved material than in the raw material, but that the same trend to greater use of the long-chain acids exists.

It is believed that the energy for the reaction is derived from the short-chain acids, while the longer-chain acids are directly taken up by the yeast.

The typical grey-white wrinkled surface skin is very easily skimmed off the substrate, and when dried is found to be about 40–50% protein. Tests have shown that the protein makes a good quality animal feed.

The amount of ammonia nitrogen in the fermentation is between 0.4% and 2.0% and optimally is about 1.3% by weight of dry fermentable matter. This gives from 0.02 to 0.1 molar total fatty acids in the liquor, dependant on the materials used, in particular the amounts of starch, cellulose and lignin contained. With 1.3% nitrogen, the digestibility of the dry matter is some 44%. At 0.8% nitrogen the digestibility is some 25%.

The yeast during growth can reduce the total carbon in effluent by 50% (3000 to 1500 p.p.m.) and dissolved carbon by 75% (1750 to 450 p.p.m.). The dissolved carbon in pig and other faecal wastes is largely responsible for the offensive ordour, which is effectively eliminated by growth of the yeast.

The pH of the liquor has some effect on the yeast growth rate. In one strain of *Candida ingens* the optimum pH was 5.3. As the process proceeds, the pH rises and yeast growth stops at pH=8.0. With a different strain of C.INGENS the corresponding pH values were 4.0 and 6.5 to 7.0. The pH of the substrate may be adjusted during the process to suit the particular yeast and increase the yield.

Tests on samples of 10 grms/l of any given yeast will give the optimum pH value, which may then be adjusted in full-scale use of that yeast.

In the fermentation of pig wastes described, dry-weight yields are of the order of 4.5 grms. per liter at 25° C. High-starch food wastes give up to 10 grms per liter.

Simple surface-skimming of the product and subsequent draining and drying at 60° C. kills the organism.

An analysis of a typical product is as follows:

Crude Protein: 44%
Riboflavine: 4.6 mg/100 g
Pantothenic Acid: 11.0 mg/100 g.
Vitamin $B_{12}$: 246 mg/100 g
Ca: 3.7%
P: 3.6%
Na: 150 ppm
K: 0.23%

Instead of raw wastes, sterile wastes may be used as a substrate, but give somewhat lower yields of essential aminoacids.

On the figures given above, if the product makes up 8% of a pig feed by weight, all the Riboflavin, Niacin, Pantothenic Acid and Vitamin $B_{12}$ necessary will be provided.

The apparatus used in carrying out the invention may first consist of known means for anaerobic fermentation, such as an overloaded septic tank, and second an open-topped container to which the fermented material is transferred.

The container is preferably shallow, to give a high ratio of surface area to contained volume, and is provided with a slow-moving stirrer which circulates the substrate to and from the surface without breaking the surface yeast layer.

Alternatively, an elongated flow-through vessel may be used to give a continuous rather than a batch output. Stirring may be by gentle recirculation of the substrate through a perforated hose lying along the bottom of such a vessel.

Very small energy mechanical inputs are therefore needed for the process.

Other specific advantages of the process over other known yeast processes are that the harvesting of the yeast protein is particularly easy and does not involve centrifuging or filtration; no aeration of the substrate is involved; the quality of the protein produced is comparable or superior to previous more expensive protein foods, such as fish meal, soy bean meal or skim milk, and shows no toxicity to animals.

That I claim is:

1. A process for producing yeast protein including the following steps:
    (a) subjecting biological waste material to anaerobic fermentation in a liquid medium to provide a yeast growth promoting substrate comprised of a mixture of volatile monocarboxylic acids;
    (b) introducing into the resultant ferment a pellicle-forming yeast selected from the group consisting of *Candida ingens* and *Pichia membranaefaciens;*
    (c) adjusting the ammonia nitrogen content of said liquid medium to a total nitrogen content of between 0.4% and 2.0% by weight of dry matter;
    (d) allowing a surface layer of said yeast to grow on said liquid medium;
    (e) gently circulating said medium beneath said surface layer without disturbing or breaking up said layer;
    (f) skimming off said layer; and
    (g) drying said skimmed yeast to form said yeast protein.

2. The process as defined in claim 1, wherein said yeast is *Candida ingens* and including the further step of adjusting the pH of the liquid medium during the process to a constant value between 4.0 and 8.0.

3. A process as defined in claim 2, in which the pH is adjusted to 5.3.

4. The process as defined in claim 1, wherein the temperature at the surface of said liquid medium is between about 25° C. and 28° C. during yeast growth.

* * * * *